United States Patent
Jiang et al.

(10) Patent No.: US 12,391,717 B2
(45) Date of Patent: Aug. 19, 2025

(54) METHOD FOR PREPARING SUCROSE-6-ESTER

(71) Applicant: ANHUI JINHE INDUSTRIAL CO., LTD., Anhui (CN)

(72) Inventors: Weiqiang Jiang, Anhui (CN); Jiaxin Xia, Anhui (CN); Zhengsong Zhang, Anhui (CN); Zhijian Yang, Anhui (CN); Chaohui Chen, Anhui (CN)

(73) Assignee: ANHUI JINHE INDUSTRIAL CO., LTD., Anhui (CN)

( * ) Notice: Subject to any disclaimer, the term of this patent is extended or adjusted under 35 U.S.C. 154(b) by 490 days.

(21) Appl. No.: 18/003,504

(22) PCT Filed: Sep. 10, 2020

(86) PCT No.: PCT/CN2020/114505
§ 371 (c)(1),
(2) Date: Dec. 28, 2022

(87) PCT Pub. No.: WO2022/051988
PCT Pub. Date: Mar. 17, 2022

(65) Prior Publication Data
US 2023/0295210 A1    Sep. 21, 2023

(51) Int. Cl.
*C07H 13/04* (2006.01)
*C07H 1/00* (2006.01)

(52) U.S. Cl.
CPC .............. *C07H 13/04* (2013.01); *C07H 1/00* (2013.01)

(58) Field of Classification Search
CPC .......... C07H 13/04; C07H 1/00; B01J 19/002; B01J 19/26
See application file for complete search history.

(56) References Cited

U.S. PATENT DOCUMENTS

| | | | |
|---|---|---|---|
| 4,950,746 A | 8/1990 | Navia | |
| 5,023,329 A | 6/1991 | Neiditch et al. | |
| 5,089,608 A | 2/1992 | Walkup et al. | |
| 6,939,962 B2 | 9/2005 | Clark et al. | |
| 8,912,320 B2 | 12/2014 | Kerr et al. | |
| 8,921,540 B2 | 12/2014 | Micinski et al. | |
| 9,073,959 B2 | 7/2015 | Micinski et al. | |
| 2003/0158404 A1 | 8/2003 | Clark et al. | |
| 2009/0105470 A1 | 4/2009 | Ratnam et al. | |
| 2011/0087018 A1 | 4/2011 | Micinski et al. | |
| 2011/0087019 A1 | 4/2011 | Micinski et al. | |
| 2012/0157676 A1 | 6/2012 | Kerr et al. | |

FOREIGN PATENT DOCUMENTS

| | | |
|---|---|---|
| CN | 1528772 A | 9/2004 |
| CN | 1210286 C | 7/2005 |
| CN | 101132705 A | 2/2008 |
| CN | 101605804 A | 12/2009 |
| CN | 102365291 A | 2/2012 |
| CN | 102627675 A | 8/2012 |
| CN | 102639550 A | 8/2012 |
| CN | 102639551 A | 8/2012 |
| CN | 103877835 A | 6/2014 |
| CN | 106632533 A | 5/2017 |
| CN | 108395876 A | 8/2018 |
| CN | 112384522 A | 2/2021 |
| EP | 0475619 A | 3/1992 |
| GB | 1387062 A | 3/1975 |
| WO | 2008084197 A1 | 7/2008 |
| WO | 2009035503 A1 | 3/2009 |

OTHER PUBLICATIONS

Wei et al., Annu. Rev. Phys. Chem., 2020, 71, p. 31-51. (Year: 2020).*
International Search Report and Written Opinion mailed May 28, 2021, in connection with International Patent Application No. PCT/CN2020/114505, 12 pgs. (including translation).
Hongying et al., "Progress in synthesis of food sweetener sucralose," 2016, Chemical Industry and Engineering Progress, vol. 35, Issue 01, pp. 227-238.
First Office Action mailed Feb. 24, 2022, in connection with Chinese Patent Application No. 202080002104.X, 25 pgs. (including translation).
Second Office Action mailed Sep. 23, 2022, in connection with Chinese Patent Application No. 202080002104.X, 29 pgs. (including translation).
"Principles of Operation of Chemical Works," Ed. Lauer Column, First Ed. Apr. 2019, Electron and Technology University Press, pp. 176-178, 6 pgs. (including translation).

* cited by examiner

*Primary Examiner* — Jonathan S Lau
(74) *Attorney, Agent, or Firm* — Chiesa Shahinian & Giantomasi PC

(57) ABSTRACT

Provided is a method for preparing a sucrose-6-ester, including: preparing a reaction solution of sucrose and an organotin compound; atomizing the reaction solution to form droplets; thoroughly mixing and contacting the droplets with a gasified dehydration medium such that the droplets undergo a dehydration reaction to obtain an intermediate mixture containing sucrose organic tin ester droplets; separating the intermediate mixture to obtain a sucrose organic tin ester solution and a dehydrated gas-liquid mixture; recovering the sucrose organic tin ester solution obtained in the separation step and cycling to the atomization and dehydration steps several times; and subjecting an organic acid anhydride to an acylation reaction with the sucrose organic tin ester solution to obtain the sucrose-6-ester.

16 Claims, 1 Drawing Sheet

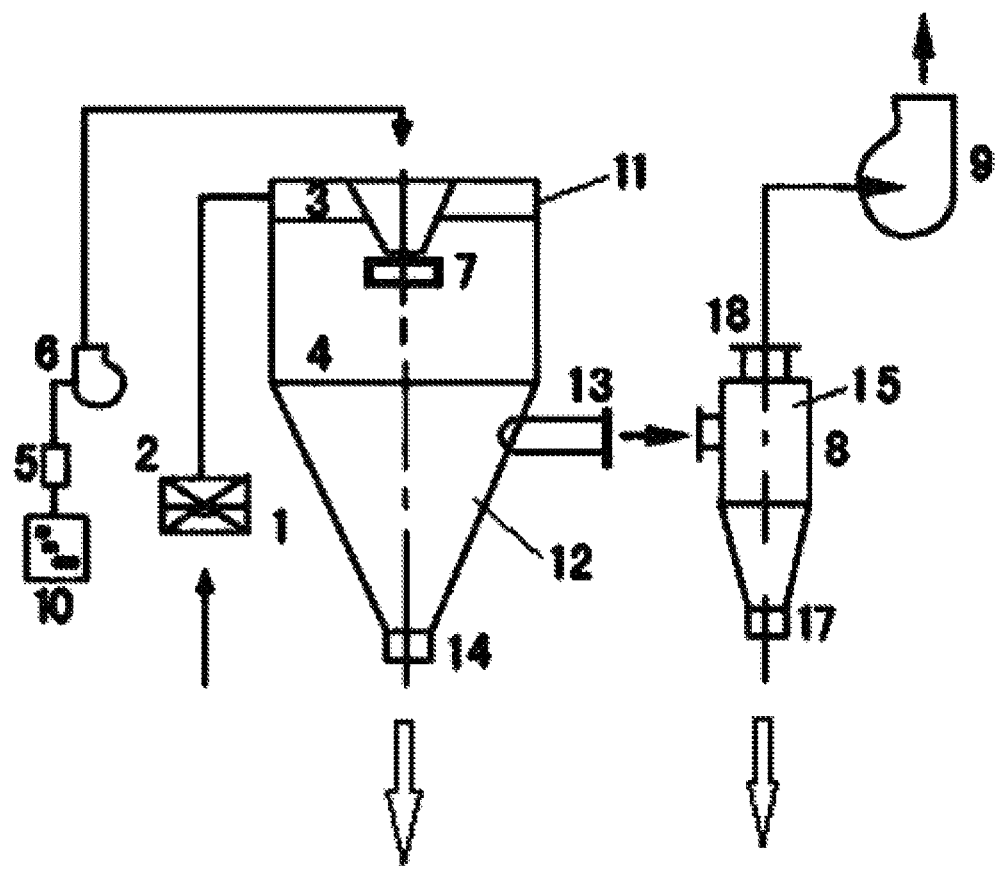

METHOD FOR PREPARING SUCROSE-6-ESTER

CROSS-REFERENCE TO RELATED APPLICATIONS

This application is a National Stage under 35 U.S.C. 371 of International Patent Application No. PCT/CN2020/114505, filed Sep. 10, 2020; the disclosure of which is incorporated herein by reference in its entirety.

TECHNICAL FIELD

The present disclosure belongs to the technical field of chemical production, and in particular to a method for preparing a sucrose-6-ester.

BACKGROUND

Sucrose-6-ester is an important chemical and intermediate. For example, sucrose-6-acetate is an important intermediate for the synthesis of sucralose (Wu Hongying, College of Chemical and Biological Engineering, Zhejiang University, Wu Hongying, et al. Progress in Synthesis of Food Sweetener Sucralose [J]. Chemical Industry and Engineering Progress, 2016, 35 (1): 227-238). Many sucrose-6-fatty acid esters are important food additives and chemicals.

At present, the sucrose-6-ester is usually synthesized by the mono-group protection method in the industry. The mono-group protection method generally comprises: dissolving an organo-tin compound and sucrose in a polar solvent, performing azeotropic dehydration with a non-polar solvent (Chinese Patent CN1210286) or direct distillation dehydration with a single polar solvent (Chinese Patent CN102639550) to obtain a sucrose organic tin ester solution, and then conducting highly selective reaction of the sucrose organic tin ester solution with an acylating agent carboxylic anhydride to obtain the sucrose-6-carboxylate.

In the current dehydration technologies for synthesizing a sucrose organic tin ester solution, due to the constrictions of esterification reaction kinetics and the characteristics of various existing dehydration technologies themselves, the dehydration reaction is relatively slow and generally takes one to a few hours. Few of the more thorough dehydration esterification reactions are completed within 1 h. The prolongation of esterification reaction time will lead to the decomposition of saccharides in the reaction system and the occurrence of side reactions, resulting in serious adverse consequences, for example, making the reaction system dark color, the subsequent solid-liquid separation (SLS) difficult, and the process operation prone to error; hindering the subsequent extraction and recovery of organic tin catalysts; reducing the content of sucrose organic tin ester in solutions and affecting the yield of a sucrose-6-ester; and directly affecting the subsequent chlorination reaction of a sucrose-6-ester and the reaction control, separation effect, and yield of a sucralose production process.

The atomization drying technology as drying technology is often used for evaporating solvents and drying materials, as disclosed in Chinese Patent CN102365291A. The atomization drying technology is a process that can be completed in a short time. One of the technical problems for the esterification dehydration reaction is how to quickly remove the generated water to avoid reverse reactions and reduce side reactions. In the prior art, it is generally considered that the esterification dehydration reaction is a reaction that needs a long time to smooth going and reach a certain reaction degree. Therefore, there is no precedent in the prior art for applying the atomization drying technology in the production of a sucrose-6-ester.

SUMMARY

In view of the above problems, the present disclosure provides a method for preparing a sucrose-6-ester which makes it possible to overcome the above problems or at least partially solve the above problems.

According to one aspect of the present disclosure, provided is a method for preparing a sucrose-6-ester, comprising:

preparation of a reaction solution: heating and dissolving sucrose and an organo-tin compound in a polar aprotic solvent, and adding a non-polar solvent thereto to obtain a reaction solution;

atomization: atomizing the reaction solution to form droplets;

dehydration: thoroughly mixing and contacting the droplets with a gasified dehydration medium such that the droplets undergo a dehydration reaction to obtain an intermediate mixture containing sucrose organic tin ester droplets;

separation: separating the intermediate mixture to obtain a sucrose organic tin ester solution and a dehydrated gas-liquid mixture;

circulation: recovering the sucrose organic tin ester solution obtained in the separation step and cycling to the atomization and dehydration steps several times; and acylation: subjecting an organic acid anhydride to an acylation reaction with the sucrose organic tin ester solution to obtain the sucrose-6-ester.

In some embodiments, the above method for preparing a sucrose-6-ester further comprises:

recycling: subjecting the dehydrated gas-liquid mixture obtained in the separation step to gas-liquid separation to obtain a liquid substance and a gaseous substance, merging the liquid substance into the sucrose organic tin ester solution, and recovering the gaseous substance.

In some embodiments, in the above method for preparing a sucrose-6-ester, in the circulation step, the cycling is conducted 2 to 10 times, preferably 3 to 5 times.

In some embodiments, in the above method for preparing a sucrose-6-ester, wherein the organo-tin compound is any one or more selected from the group consisting of 1,3-dihydrocarbyloxy-1,1,3,3-tetra-(hydrocarbyl)distannoxane, tin di(hydrocarbyl)oxide, 1,3-diacyloxy-1,1,3,3-tetra-(hydrocarbyl)distannoxane, and 1-acyloxy-1,1,3,3-tetra-(hydrocarbyl)distannoxane, preferably 1,3-diacyloxy-1,1,3,3-tetra-(hydrocarbyl)distannoxane, and more preferably 1,3-diacetoxy-1,1,3,3-tetrabutyldistannoxane; wherein the hydrocarbyloxy is selected from the group consisting of alkoxy and phenoxy; the alkoxy is preferably selected from the group consisting of methoxy, ethoxy, n-propoxy, n-butoxy, n-pentoxy, and n-hexoxy, and more preferably methoxy; the hydrocarbyl is selected from the group consisting of alkyl, cycloalkyl, aryl, and aralkyl, preferably alkyl, and more preferably n-butyl;

the polar aprotic solvent is any one or more selected from the group consisting of dimethyl sulfoxide (DMSO), N-methylpyrrolidone (NMP), N,N-dimethylacetamide (DMA), hexamethylphosphoramide (HMPA), and N,N-dimethylformamide (DMF), preferably DMF; and the non-polar solvent is any one selected from the group consisting of cyclohexane, hexane, n-heptane, iso-octane, benzene, toluene, chloroform, carbon tetrachloride, hexane, ethyl acetate, and methyl acetate, preferably any one selected from the group consisting of cyclohexane, hexane, and n-heptane, and more preferably cyclohexane.

In some embodiments, in the above method for preparing a sucrose-6-ester, wherein based on a mass of sucrose, a ratio of a mass of the organo-tin compound to the mass of sucrose is a range of 0.3-3.0, preferably 0.5-2.0, and more preferably 0.9-1.2;
  based on the mass of sucrose, a ratio of a volume of the polar aprotic solvent to the mass of sucrose is within a range of 2-20, preferably 3-10, and more preferably 4-8; and
  based on the volume of the polar aprotic solvent, a volume of the non-polar solvent is less than 30% of the volume of the polar aprotic solvent, preferably 20%, and more preferably 15%.

In some embodiments, in the above method for preparing a sucrose-6-ester, wherein in the atomization, atomizing the reaction solution to form droplets comprises:
  heating the reaction solution to 70° C. to 120° C., preferably 80° C. to 100° C., and pressurizing to 0.01 MPa to 3 MPa for atomization to form droplets, wherein a number of the droplets with a particle size less than 10 μm in the droplets accounts for 90% or more of a total number of the droplets.

In some embodiments, in the above method for preparing a sucrose-6-ester, wherein the dehydration medium is selected from the group consisting of nitrogen and a non-polar solvent, wherein the non-polar solvent is any one selected from the group consisting of cyclohexane, hexane, n-heptane, iso-octane, benzene, toluene, chloroform, carbon tetrachloride, hexane, ethyl acetate, and methyl acetate, preferably any one selected from the group consisting of cyclohexane, hexane, and n-heptane, and more preferably cyclohexane;
  based on a total mass of sucrose, the polar aprotic solvent, and the polar aprotic solvent, a ratio of a mass of the dehydration medium to the total mass is within a range of 100:0.1 to 0.1:1, preferably 20:1 to 1:1;
  the dehydration medium has a gasification temperature of 80° C. to 160° C., preferably 100° C. to 120° C., and a gasification pressure of 0.01 MPa to 3.0 MPa, preferably 0.05 MPa to 0.2 MPa; and
  a contact time between the droplets and the gasified dehydration medium is 1 s to 10 min, preferably 1 min to 5 min.

In some embodiments, in the above method for preparing a sucrose-6-ester, wherein the organic acid anhydride is any one selected from the group consisting of acetic anhydride, butyric anhydride, benzoic anhydride, stearic anhydride, and lauric anhydride;
  based on the mass of sucrose, a ratio of a mass of the organic acid anhydride to the mass of sucrose is in a range of 0.6-3.0, preferably 0.8-1.5; and
  the acylation reaction is conducted at a temperature of 0° C. to 50° C., preferably 5° C. to 20° C.

According to another aspect of the present disclosure, provided is a method for preparing a sucrose-6-ester, wherein in the method, an atomization dehydration reactor is used, and the atomization dehydration reactor comprises a reactor body that is provided with a drying chamber and a first discharge chamber sequentially from top to bottom; the drying chamber is provided with an atomization nozzle, and the atomization nozzle is connected with a liquid material tank through an on-line heater and an infusion pressure pump successively; a top of the drying chamber is further provided with a gas distributor, and a vaporizer equipped with a gas filter is connected to an inlet of the gas distributor; and one end of the first discharge chamber is provided with a first gas discharge pipe, and the other end is provided with a first liquid discharge port; and
  the method comprises:
    preparation of a reaction solution: heating and dissolving sucrose and an organo-tin compound in a polar aprotic solvent, and adding a non-polar solvent thereto to obtain a reaction mixed solution;
    atomization: adding the reaction mixed solution to the liquid material tank, heating by the on-line heater and pressurizing by the infusion pressure pump, introducing into the atomization nozzle and atomizing into droplets, and spraying the droplets into the drying chamber;
    dehydration: adding a dehydration medium to the vaporizer, filtering, heating, and pressurizing to form a gasified dehydration medium, and introducing the gasified dehydration medium into the gas distributor, evenly distributing by the gas distributor, and introducing into the drying chamber,
    wherein the droplets and the gasified dehydration medium are thoroughly mixed and contacted in the drying chamber, such that the droplets undergo a dehydration reaction to obtain an intermediate mixture containing sucrose organic tin ester droplets;
    separation: subjecting the intermediate mixture to gas-liquid separation in the first discharge chamber to obtain a sucrose organic tin ester solution and a dehydrated gas-liquid mixture. discharging the sucrose organic tin ester solution from the first liquid discharge port of the first discharge chamber, and discharging and recovering the dehydrated gas-liquid mixture from the first gas discharge pipe of the first discharge chamber;
    circulation: recovering the sucrose organic tin ester solution obtained in the separation step to the liquid material tank, such that the sucrose organic tin ester solution is cycled through the atomization and dehydration steps several times;
    or,
    a plurality of the atomization dehydration reactors are sequentially provided in series at the first liquid discharge port arranged at the other end of the first discharge chamber, and after being discharged from the first liquid discharge port of the first discharge chamber, the sucrose organic tin ester solution successively passes through the plurality of atomization dehydration reactors provided in series, such that the sucrose organic tin ester solution is cycled through the atomization and dehydration steps; and
    acylation: subjecting an organic acid anhydride to an acylation reaction with the sucrose organic tin ester solution to obtain the sucrose-6-ester.

In some embodiments, in the above method for preparing a sucrose-6-ester, the atomization dehydration reactor further comprises a cyclone separator, and the gas discharge pipe of the first discharge chamber is connected to an inlet of the cyclone separator; the cyclone separator is provided with a separation chamber and a second discharge chamber sequentially from top to bottom; one end of the separation chamber is provided with a gas outlet that is connected to an induced drag fan; and the second discharge chamber is provided with a second liquid discharge port; and
  the method further comprises:

recycling: subjecting the dehydrated gas-liquid mixture obtained in the separation step to gas-liquid separation to obtain a liquid substance and a gaseous substance, merging the liquid substance into the sucrose organic tin ester solution, and recovering the gaseous substance.

In some embodiments, in the above method for preparing a sucrose-6-ester, in the circulation step, the cycling is conducted 2 to 10 times, preferably 3 to 5 times.

In summary, the present disclosure has the following beneficial effects:

In the present disclosure, a sucrose-6-ester is prepared by the atomization drying method. The droplets atomized by the reaction solution have a huge specific surface area (SSA), such that the rapid and efficient dehydration of the esterification reaction can be achieved in a very short period of time, the sucrose organic tin ester intermediate can be efficiently prepared, and the decomposition of saccharides in a system and the occurrence of side reactions can be greatly reduced. Through repeated cyclic dehydration reactions of the sucrose organic tin ester solution, the product has a high yield and strong selectivity, the sucrose reaction degree is more thorough, and the conversion degree of sucrose is obviously improved. Moreover, the overall energy consumption of the reaction is low and the energy consumption is significantly saved. Thus, the method makes it possible to overcome the shortcomings of the traditional methods for preparing a sucrose-6-ester, such as a long time, high energy consumption, many side reactions, complicated operations, and low yield, and is especially suitable for large-scale industrial production.

The above description is merely a summary of the technical solutions of the present disclosure. In order to allow the technical means of the present disclosure to be understood clearly and implemented in accordance with the content of the specification and allow the above and other objectives, features, and advantages of the present disclosure to be obvious and easy to understand, specific implementations of the present disclosure are described below.

BRIEF DESCRIPTION OF THE DRAWINGS

Various other advantages and benefits will become clear to those of ordinary skill in the art by reading the detailed description of the following preferred embodiments. The drawings are merely for the purpose of illustrating the preferred embodiments, rather than being considered to limit the present disclosure. The same reference numerals represent the same component throughout the drawings. In the drawings:

FIG. 1 shows a schematic structural diagram of the atomization dehydration reactor according to an embodiment of the present disclosure.

DETAILED DESCRIPTION OF THE EMBODIMENTS

Exemplary embodiments of the present disclosure will be described in detail below with reference to the drawings. Although the drawings show exemplary embodiments of the present disclosure, it should be understood that the present disclosure may be implemented in various forms and should not be limited to the embodiments set forth herein. Instead, these embodiments are provided to enable a more thorough understanding of the present disclosure, and the scope of the present disclosure can be fully conveyed to those skilled in the art.

The technical solutions provided in various embodiments of the present disclosure will be described in detail below with reference to the following drawings.

The concept of the present disclosure is as follows:

At present, in the prior art, the esterification reaction time of the intermediate product sucrose organic tin ester produced from the preparation of a sucrose-6-ester is generally 3 h to 4 h or more, which causes a large number of side reactions. In view of the above defects, in the present disclosure, the formation reaction of the sucrose organic tin ester is improved by the atomization dehydration reaction, which makes the dehydration process rapid and efficient, promotes the fast forward progress of the reaction, reduces the decomposition of saccharides in the reaction system and the occurrence of side reactions, improves the dehydration efficiency and reduces the content of unreacted sucrose, thereby improving the selectivity and yield of the reaction.

The present disclosure provides a method for preparing a sucrose-6-ester, comprising: preparation of a reaction solution: adding and dissolving sucrose and an organo-tin compound in a polar aprotic solvent, and adding a non-polar solvent thereto to obtain a reaction solution; atomization: atomizing the reaction solution to form droplets; dehydration: thoroughly mixing and contacting the droplets with a gasified dehydration medium such that the droplets undergo a dehydration reaction to obtain an intermediate mixture containing sucrose organic tin ester droplets; separation: separating the intermediate mixture to obtain a sucrose organic tin ester solution and a dehydrated gas-liquid mixture; circulation: recovering the sucrose organic tin ester solution obtained in the separation step and cycling to the atomization and dehydration steps several times; and acylation: subjecting an organic acid anhydride to an acylation reaction with the sucrose organic tin ester solution to obtain the sucrose-6-ester.

The atomization drying technology is widely used in the chemical industry, light industry, food industry, and other industries due to its advantages of fast and efficient drying, and the atomization drying technology is most commonly used in the dye industry in the chemical industry. In the atomization drying technology, hot air is usually introduced into the top of a drying tower, and a feed liquid is also fed to the top of the tower and sprayed by an atomizer into mist droplets; these droplets have a very large surface area, and after contacted with high-temperature hot air, the moisture is quickly evaporated, such that a dry product is obtained in a very short period of time; the hot air discharged from the bottom of the drying tower contacts with the droplets, such that the temperature of the hot air decreases significantly and the humidity of the hot air increases; and the resulting gas is exhausted as an exhaust gas by an exhaust fan, and particles entrained in the exhaust gas are recovered by a separation device. The atomization drying technology has the following applied characteristics: 1) fast drying speed; 2) the quality of the material will not be affected by a high-temperature gas, and the product has good dispersion, fluidity, and solubility; 3) the production process is simple, the operation and control are convenient, and the automation is easy to realize; 4) suitable for continuous large-scale production; and 5) the heat-sensitive materials, biological products, and pharmaceutical products can be dried under near vacuum.

In the prior art, the esterification reaction time of the sucrose organic tin ester is generally 3 h to 4 h or more, and the generated moisture cannot be quickly removed from the reaction system, which causes the occurrence of a large number of side reactions and a low sucrose conversion degree. Due to the above characteristics of the atomization drying technology, it is found in the present disclosure that the atomization drying technology can be applied to the sugar and organic tin-containing solution with high viscosity involved in the present disclosure, and enables the two to be completely dehydrated in a short period of time, which avoids the occurrence of a large number of side reactions and improves the selectivity of the sucrose-6-ester.

Specifically, the reaction principle of the present disclosure is as follows:

Since the solution of sucrose and organo-tin compound is atomized into extremely-small droplets with a very large SSA, it is very easy to realize heat transfer and mass transfer, and the moisture inside the micron droplets is very easily exchanged into the gasified dehydration medium; that is, the water produced by the esterification reaction inside the micron droplets is taken away. After the gas-liquid separation, a dehydrated sucrose organic tin ester solution is obtained.

In addition, the sucrose organic tin ester solution cannot be completely dehydrated after a dehydration reaction. In order to further improve the reaction degree and achieve the ideal esterification effect, the present disclosure designs a circulation step, such that the sucrose organic tin ester solution can be repeatedly subjected to an atomization drying dehydration reaction many times to obtain a completely-dehydrated sucrose organic tin ester solution, thereby achieving an efficient, rapid, and continuous dehydration effect. Therefore, the multiple dehydration reaction mode can achieve the rapid and efficient dehydration reaction in a continuous way, which can greatly improve the production efficiency, realize the large-scale operation, increase the operability of the process, reduce the number of reactors and simplify the production process to achieve a higher automation level, and reduce the energy consumption and operation cost, thereby achieving the purpose of large-scale industrial production.

In some embodiments of the present disclosure, the above method for preparing a sucrose-6-ester further comprises: recycling: subjecting the dehydrated gas-liquid mixture obtained in the separation step to gas-liquid separation, merging the resulting liquid substance into the sucrose organic tin ester solution, and recovering the resulting gaseous substance.

With only one gas-liquid separation operation, it is difficult to complete the gas-liquid separation. Thus, a small part of the droplets containing sucrose organic tin ester will be mixed with water vapor into the gasified dehydration medium and then leave the reaction system together with the dehydration medium, which causes a waste of reaction raw materials. Therefore, in some embodiments, the method further comprises: recycling: specifically, subjecting the dehydrated gas-liquid mixture obtained in the separation step to gas-liquid separation, merging the resulting liquid substance into the sucrose organic tin ester solution, and recovering the resulting gaseous substance.

In some embodiments of the present disclosure, in the method for preparing a sucrose-6-ester, the cycling in the cycling step is conducted 2 to 10 times, preferably 3 to 5 times.

The multiple cycle reaction can make the sucrose organic tin ester solution be continuously subjected to multiple reactions to achieve a complete dehydration effect. In the present disclosure, there is no limitation on the number of dehydration reaction cycles. In some embodiments, the number of dehydration reaction cycles is in a range of 2-10. In some other embodiments, the number of dehydration reaction cycles is in a range of 3-5. If the number of cycles is less than 2, the dehydration cannot be completely carried out and the degree of the esterification reaction of sucrose is insufficient; if the number of cycles is more than 10, at this time, the dehydration degree of sucrose is already complete, and the continued dehydration will cause unnecessary waste and even cause deep dehydration of sucrose to form by-products such as caramel, and may even cause charring and coking in severe cases.

Type and Amount of the Organo-Tin Compound

In some embodiments of the present disclosure, there is no limitation on the types of organo-tin compound, and a monotin organic compound or a bitin organic compound may be used. In some embodiments, the organo-tin compound is any one or more selected from the group consisting of 1,3-dihydrocarbyloxy-1,1,3,3-tetra-(hydrocarbyl)distannoxane, tin di(hydrocarbyl)oxide, 1,3-diacyloxy-1,1,3,3-tetra-(hydrocarbyl)distannoxane, and 1-acyloxy-1,1,3,3-tetra-(hydrocarbyl)distannoxane. In some other embodiments, the organo-tin compound is 1,3-diacyloxy-1,1,3,3-tetra-(hydrocarbyl)distannoxane. In some other embodiments, the organotin compound is 1,3-diacetoxy-1,1,3,3-tetrabutyldistannoxane. In some embodiments, the hydrocarbyloxy is selected from the group consisting of alkoxy and phenoxy; the alkoxy is selected from the group consisting of methoxy, ethoxy, n-propoxy, n-butoxy, n-pentoxy, and n-hexoxy; when the alkoxy is methoxy, a prominent effect can be achieved. In some embodiments, the hydrocarbyl is selected from the group consisting of alkyl, cycloalkyl, aryl, and aralkyl. In some other embodiments, the hydrocarbyl is alkyl; when the hydrocarbyl is n-butyl, a prominent effect can be achieved.

In some embodiments of the present disclosure, there is no limitation on the amount of the organo-tin compound. It is recommended that, based on a mass of sucrose, a ratio of a mass of the organo-tin compound to the mass of sucrose is in a range of 0.3-3.0. In some embodiments, the ratio of the mass of the organo-tin compound to the mass of sucrose is in a range of 0.5-2.0. In some other embodiments, the ratio of the mass of the organo-tin compound to the mass of sucrose is in a range of 0.9-1.2. If the mass of the organo-tin compound is less than 30% of the mass of sucrose, the amount is too small, and a large amount of sucrose will remain in the reaction system and cannot participate in the reaction, which is not conducive to the forward progress of the reaction; if the mass of the organo-tin compound is more than 300% of the mass of sucrose, the amount is too much, a diesterification or polyesterification reaction will occur.

Type and Amount of the Polar Aprotic Solvent

In some embodiments of the present disclosure, there is no limitation on the type of the polar aprotic solvent. The polar aprotic solvent is any one or more selected from the group consisting of DMSO, NMP, DMA, HMPA, and DMF. In some embodiments, DMF is recommended as the polar aprotic solvent.

In some embodiments of the present disclosure, there is no limitation on the amount of the polar aprotic solvent. Based on the mass of sucrose, a ratio of a mass of the polar aprotic solvent to the mass of sucrose is in a range of 2-20. In some embodiments, the ratio of the mass of the polar aprotic solvent to the mass of sucrose is in a range of 3-10. In some other embodiments, the ratio of the mass of the polar aprotic solvent to the mass of sucrose is in a range of 4-8. If the mass of the polar aprotic solvent is less than 200% of the mass of sucrose, the amount is too small, and sucrose cannot be completely dissolved, resulting in a waste of a part of the sucrose raw material, which will affect the heat transfer and mass transfer in the subsequent reaction process because sucrose exists in solid form. If the mass of the polar aprotic solvent is more than 2000% of the mass of the sucrose, the amount is too much, resulting in a waste of the raw material, which brings great troubles to the subsequent solvent treatment and even causes excessive energy consumption, increased production costs, reduced efficiency, and environmental pollution.

Type and Amount of the Non-Polar Solvent

In some embodiments of the present disclosure, there is no limitation on the type of the non-polar solvent. The non-polar solvent is any one selected from the group consisting of cyclohexane, hexane, n-heptane, iso-octane, benzene, toluene, chloroform, carbon tetrachloride, hexane, ethyl acetate, and methyl acetate. In some embodiments, the non-polar solvent is any one selected from the group consisting of cyclohexane, hexane, and n-heptane. In some embodiments, cyclohexane is recommended as the non-polar solvent.

In some embodiments of the present disclosure, there is no limitation on the amount of the non-polar solvent. Based on the volume of the polar aprotic solvent, a volume of the non-polar solvent is less than 30% of the volume of the polar aprotic solvent. In some embodiments, the volume of the non-polar solvent is less than 20% of the volume of the polar aprotic solvent. In some other embodiments, the volume of the non-polar solvent is less than 15% of the volume of the polar aprotic solvent. The role of the non-polar solvent here is to improve the subsequent atomization effect. If the volume of the non-polar solvent is greater than 30% of the volume of the polar aprotic solvent, the volume is too much, which will cause problems such as too-high non-polarity, difficult sucrose dissolution, and solid precipitation.

Type and Amount of the Dehydration Medium and Gasification Conditions of the Dehydration Medium In some embodiments of the present disclosure, there is no limitation on the type of the dehydration medium. The dehydration medium is selected from the group consisting of nitrogen and a non-polar solvent, wherein when the dehydration medium is a non-polar solvent, the non-polar solvent is any one selected from the group consisting of cyclohexane, hexane, n-heptane, iso-octane, benzene, toluene, chloroform, carbon tetrachloride, hexane, ethyl acetate, and methyl acetate. In some embodiments, the non-polar solvent is any one selected from the group consisting of cyclohexane, hexane, and n-heptane. In some other embodiments, cyclohexane is recommended as the non-polar solvent.

In some embodiments of the present disclosure, there is no limitation on the amount of the dehydration medium. Based on a total mass of the sucrose, the polar aprotic solvent, and the polar aprotic solvent, a ratio of the mass of the dehydration medium to the total mass is within a range 100:0.1 to 0.1:1. In some embodiments, the ratio of the mass of the dehydration medium to the total mass is within a range 20:1 to 1:1. If the amount of the dehydration medium is less than the minimum value of the above ratio range, the amount is too low, which leads to the dehydration medium not completely taking away the water vapor generated by the esterification reaction, and cannot play an effective role in promoting the forward progress of the reaction; if the amount of the dehydration medium is more than the maximum value of the above ratio range, the amount is too much, which causes unnecessary waste under the condition that the water vapor can be completely taken away.

In some embodiments of the present disclosure, there is no limitation on the gasification conditions of the dehydration medium. The dehydration medium has a gasification temperature of 80° C. to 160° C. In some embodiments, the dehydration medium has a gasification temperature of 100° C. to 120° C.; and the dehydration medium has a gasification pressure of 0.01 MPa to 3.0 MPa. In some embodiments, the dehydration medium has a gasification pressure of 0.05 MPa to 0.2 MPa. The gasification conditions of the dehydration medium may be determined according to the type of the dehydration medium, the boiling point of the dehydration medium, and the needs of the reaction.

Atomization Conditions of the Reaction Solution

In some embodiments of the present disclosure, there is no limitation on the atomization conditions of the reaction solution. In some embodiments, the following atomization conditions are recommended: heating the reaction solution to 70° C. to 120° C. (80° C. to 100° C. in some other embodiments), and pressurizing to 0.01 MPa to 3 MPa for atomizing to obtain the droplets, wherein a number of the droplets with a particle size less than 10 μm in the droplets accounts for 90% or more of a total number of the droplets.

The atomization is a relatively critical step to ensure the smooth generation of sucrose organic tin ester solution in the present disclosure. The accurate control of the atomization conditions allows the reaction solution to generate a large number of droplets with a suitable size. The huge surface area of the droplets is a key factor to ensure the smooth progress of the reaction, which can be achieved by the above recommended atomization conditions. When the heating temperature of the reaction solution is lower than 70° C. and the pressure is lower than 0.01 MPa, the temperature is too low and the pressure is too low, and the dehydration medium cannot be quickly atomized; if the heating temperature is higher than 100° C. and the pressure is higher than 3 MPa, the temperature is too high, and the dehydration medium will be atomized too fast such that the operation is difficult to control, and the pressure of an atomization device will be increased instantaneously, which may cause potential hazards.

Reaction Conditions of the Dehydration Reaction

In some embodiments of the present disclosure, there is no limitation on the reaction conditions for the dehydration medium. The dehydration reaction is conducted for 1 s to 10 min, preferably 1 min to 5 min. Since the atomization drying reaction mode is used in the present disclosure, the esterification reaction time is greatly shortened. In the present disclosure, the esterification dehydration reaction can be conducted completely within 1 s to 10 min. In some embodiments, the esterification dehydration reaction can be conducted completely within 1 min to 5 min, which greatly avoids the occurrence of side reactions such as sucrose decomposition. The esterification reaction time is much shorter than that of the prior art.

Type and Amount of the Organic Acid Anhydride and Reaction Conditions of the Acylation Reaction In some embodiments of the present disclosure, there is no limitation on the type of the organic acid anhydride. The organic acid anhydride may be any one selected from the group consisting of acetic anhydride, butyric anhydride, benzoic anhydride, stearic anhydride, and lauric anhydride. The sucrose organic tin ester solution is subjected to an acylation reaction with carboxylic anhydride after being cooled to obtain a sucrose-6-ester. According to the types of the above organic acid anhydrides, the corresponding sucrose-6-esters are sucrose-6-acetate, sucrose-6-butyrate, sucrose-6-benzoate, sucrose-6-fatty acid ester, and sucrose-6-laurate. The sucrose-6-acetate and sucrose-6-benzoate obtained in the present disclosure can be used as the intermediates of synthesizing a sweetener sucralose, and the other types of sucrose-6-carboxylate can be used as food additives, chemical products, and synthetic intermediates for other reactions.

In some embodiments of the present disclosure, there is no limitation on the amount of the organic acid anhydride. Based on the mass of the sucrose, a ratio of the mass of the organic acid anhydride to the mass of sucrose is in a range of 0.6 to 3.0. In some embodiments, the ratio of the mass of the organic acid anhydride to the mass of sucrose is in a range of 0.8 to 1.5. If the amount of the organic acid anhydride is less than the minimum value of the above ratio range, the amount is too low, the sucrose organic tin ester solution cannot be completely converted into the sucrose-6-ester; if the amount of the organic acid anhydride is more than the maximum value of the above ratio range, the amount is too much, other side reactions such as condensation may occur, resulting in complicated products and difficult purification.

In the present disclosure, there is no limitation on the reaction conditions of the acylation reaction. In some embodiments of the present disclosure, the acylation reaction is conducted at a temperature of 0° C. to 50° C., preferably 5° C. to 20° C.; and the acylation reaction is conducted for 10 min to 24 h, preferably 30 min to 4 h.

The present disclosure also provides an atomization dehydration reactor suitable for the esterification reaction between sucrose and an organo-tin compound, as shown in FIG. 1. FIG. 1 shows a schematic structural diagram of the atomization dehydration reactor according to an embodiment of the present disclosure. As shown in FIG. 1, the atomization dehydration reactor comprises a reactor body 11 that is provided with a drying chamber 4 and a first discharge chamber 12 sequentially from top to bottom the drying chamber 4 is provided with an atomization nozzle 7, and the atomization nozzle 7 is connected with a liquid material tank 10 through an on-line heater 5 and an infusion pressurized pump 6 successively; a top of the drying chamber 4 is further provided with a gas distributor 3, and a vaporizer 2 equipped with a gas filter 1 is connected to an inlet of the gas distributor 3; and one end of the first discharge chamber 12 is provided with a first gas discharge pipe 13, and the other end is provided with a first liquid discharge port 14.

When the method for preparing a sucrose-6-ester provided in the present disclosure is carried out in the atomization dehydration reactor, the method may comprise:

Preparation of a reaction mixed solution: sucrose and an organo-tin compound are heated and dissolved in a polar aprotic solvent, and a non-polar solvent is added thereto to obtain a reaction mixed solution. The addition of the non-polar solvent is intended to increase the subsequent atomization dehydration effect. Atomization: the reaction mixed solution is added to the liquid material tank 10, heated by the on-line heater 5 and pressurized by the infusion pressurized pump 6, and introduced into the atomization nozzle 7 and atomized into droplets, and the droplets are sprayed into the drying chamber 4. Dehydration: a dehydration medium is added to the vaporizer 2, filtered through a filter 1, heated, and pressurized to form a gasified dehydration medium, and the gasified dehydration medium is introduced into the gas distributor 3, and evenly distributed by the gas distributor 3, then introduced into the drying chamber 4, where the droplets and the gasified dehydration medium are thoroughly mixed and contacted with each other in the drying chamber 4, such that the droplets undergo a dehydration reaction to obtain an intermediate mixture containing sucrose organic tin ester droplets. Separation: the intermediate mixture is subjected to gas-liquid separation in the first discharge chamber 12 to obtain a sucrose organic tin ester solution and a dehydrated gas-liquid mixture; the sucrose organic tin ester solution is discharged from the first liquid discharge port 14 of the first discharge chamber 12; and the dehydrated gas-liquid mixture is discharged from the first gas discharge pipe 13 of the first discharge chamber 12 and recovered. Circulation: The sucrose organic tin ester solution obtained in the separation step is recovered and cycled to the atomization and dehydration steps. Acylation: the sucrose organic tin ester solution is subjected to an acylation reaction with an organic acid anhydride to obtain the sucrose-6-ester.

In some embodiments of the present disclosure, the sucrose organic tin ester solution obtained in the separation step is recovered and cycled to the atomization and dehydration steps, and the cycling is conducted 2 to 10 times, preferably 3 to 5 times. In this way, the sucrose organic tin ester solution can be continuously reacted many times, such that a multi-stage rapid dehydration reactor can be used to achieve thorough dehydration. In some embodiments, the number of dehydration reaction cycles is in a range of 2 to 10. In some other embodiments, the number of dehydration reaction cycles is in a range of 3 to 5. The rapid and efficient dehydration can be realized in a continuous way through the multiple reaction mode.

In some embodiments, a specific implementation may also be as follows: the sucrose organic tin ester solution obtained in the separation step is recovered to the liquid material tank 10, such that the sucrose organic tin ester solution can be circulated for the atomization and dehydration steps, and the number of cycles is 2 to 10 times, preferably 3 to 5 times. In some other embodiments, a specific implementation may also be as follows: a plurality of atomization dehydration reactors are sequentially provided in series at the first liquid discharge port 14 arranged at the other end of the first discharge chamber 12; after being discharged from the first liquid discharge port 14 of the first discharge chamber 12, the sucrose organic tin ester solution successively passes through the plurality of atomization dehydration reactors in series, such that the sucrose organic tin ester solution can be circulated for the atomization and dehydration steps, and the number of cycles is 2 to 10 times, preferably 3 to 5 times.

The multiple cycle reaction can make the sucrose organic tin ester solution be continuously subjected to multiple reactions to achieve a complete dehydration effect. In the present disclosure there is no limitation on a number of dehydration reaction cycles. In some embodiments, the number of dehydration reaction cycles is in a range of 2-10. In some other embodiments, the number of dehydration reaction cycles is in a range of 3-5. If the number of cycles is less than 2, the dehydration cannot be completely carried out and the degree of the esterification reaction of sucrose is insufficient; if the number of cycles is more than 10, at this time, the dehydration degree of sucrose is already complete, and the continued dehydration will cause unnecessary waste and even cause deep dehydration of sucrose to form by-products such as caramel, and may even cause charring and coking in severe cases.

In some embodiments of the present disclosure, a multi-stage atomization dehydration reactor is used instead of the previous batch or semi-continuous reactor, which can greatly improve the production efficiency, realize large-scale operation, increase the operability of the process, reduce the number of reactors and simplify the production process to achieve a high automation level, and reduce the energy consumption and operation cost, thereby achieving the purpose of large-scale industrial production.

In some embodiments of the present disclosure, the atomization dehydration reactor further comprises a cyclone separator 8, and the gas discharge pipe 13 of the first discharge chamber 12 is connected to an inlet of the cyclone separator 8; the cyclone separator is provided with a separation chamber 15 and a second discharge chamber 16 sequentially from top to bottom; one end of the separation chamber is provided with a gas outlet 18 that is connected to an induced drag fan 9; and the other end of the second discharge chamber 16 is provided with a second liquid discharge port 17.

When the preparation method provided in the present disclosure is carried out on the reactor provided with the cyclone separator, the preparation method further comprises: recycling: subjecting the dehydrated gas-liquid mixture obtained in the separation step to gas-liquid separation, merging the resulting liquid substance into the sucrose organic tin ester solution, and recovering the resulting gaseous substance.

With only one gas-liquid separation operation, it is difficult to complete the gas-liquid separation. Thus, a small part of the containing sucrose organic tin ester droplets will be mixed with water vapor into the gasified dehydration medium and then leave the reaction system together with the dehydration medium, which causes a waste of reaction raw materials. Therefore, in some embodiments, the preparation method further comprises: recycling: specifically, subjecting the dehydrated gas-liquid mixture obtained in the separation step to gas-liquid separation, merging the resulting liquid substance into the sucrose organic tin ester solution, and recovering the resulting gaseous substance.

In some embodiments of the present disclosure, the atomization dehydration reactor is used to realize the rapid dehydration of the esterification reaction. In order to ensure the stability of heat-sensitive substances, a vacuum negative-pressure device, such as an induced drag fan 9, may be connected to the gas outlet of the reactor body or the cyclone separator which can keep the drying chamber or separation chamber in a negative-pressure state. The negative pressure may be in a range of 0.01 kPa to 100 kPa. In some embodiments, the negative pressure may be in a range of 0.5 kPa to 90 kPa.

Thus, when the preparation method provided in the present disclosure is carried out on the above device, in some embodiments of the present disclosure, the reaction process can also be described as follows: 1) heating and dissolving sucrose and an organo-tin compound in a polar aprotic solvent to obtain a solution; 2) adding a small amount of a non-polar solvent into the solution to increase the subsequent atomization dehydration effect; 3) rapidly heating the solution of sucrose and the organo-tin compound, pressurizing, delivering to the atomization nozzle at the top of the atomization dehydration reactor and atomizing; 4) at the same time, heating the dehydration medium, introducing into the gas distributor at the top of the rapid dehydration reactor, uniformly distributing, and introducing into the drying chamber; 5) atomizing the reaction solution of sucrose and the organo-tin compound and thoroughly mixing with the dehydration medium in the drying chamber for rapid heat exchange and dehydration reaction; 6) discharging micron droplets containing the reaction solution of sucrose and the organo-tin compound obtained after the exchange from the first separation chamber and the liquid outlet of the cyclone separator and collecting to obtain a sucrose organic tin ester solution; 7) introducing the sucrose organic tin ester solution into the following multi-stage atomization dehydration reactor in series and undergoing repeated rapid dehydration to obtain a qualified sucrose organic tin ester solution; 8) outputting the dehydration medium gas obtained after the exchange from the atomization dehydration reactor by the induced drag fan or vacuum machine, and recovering the solvent, a small amount of sucrose organic tin ester, and entrained moisture therein by a pressurization, condensation, or membrane separation technique for purification, and recycling after the purification; and 9) cooling the sucrose organic tin ester solution obtained, and reacting with carboxylic anhydride to obtain a sucrose-6-carboxylate with highly-selective. Accordingly, the present disclosure provides a method for rapid dehydration by an atomization dehydration reactor technology to prepare sucrose organic tin ester, which can achieve an efficient, rapid, and continuous reaction.

The atomization dehydration reactor provided in the present disclosure is a continuous dehydration reactor. This reactor is used instead of the previous batch or semi-continuous reactor to achieve a rapid, efficient, and continuous reaction, which can greatly improve the production efficiency, increase the operability of the process, achieve a high automation level, and reduce the manual operation complexity, energy consumption, and production cost, thereby achieving the purpose of large-scale industrial production.

Example 1

1,000 g of sucrose and 2,000 g of 1,3-diacetoxy-1,1,3,3-tetra-(butyl)distannoxane were dissolved in 10 L of DMF (a polar aprotic solvent), and then 1 L of cyclohexane (a non-polar solvent) was supplemented, obtaining a reaction solution of sucrose and an organo-tin compound.

The specific process parameters of this example were as follows: atomization dehydration reactor: low-temperature vacuum spray dryer, with a model of JOYN-1000T; liquid material injection volume: 10 mL/min; atomization nozzle caliber: 0.5 mm; temperature of fed reaction solution: 80° C.; nitrogen injection volume of a vaporizer: 2,000 mL/min, temperature: 120° C.; and the system pressure in the atomization dehydration reactor: 50 KPa.

After the first reaction, the solution received at the liquid outlet was light-amber, which was a sucrose organic tin ester solution. A part of the received solution was subjected to a second atomization and dehydration operation, which was a second esterification reaction. The remaining part of the received solution was subjected to an acylation experiment. The solution obtained after the second esterification reaction was treated repeatedly as above, obtaining a third esterification reaction product. The second esterification reaction product and the third esterification reaction product were each subjected to an acylation experiment, and the composition and content of the resulting products were tested.

The sugar content of the sucrose organic tin ester solution obtained after the dehydration reaction was calculated by high-performance liquid chromatography (HPLC) testing. The solution volume corresponding to the same sugar content was calculated. Acetic anhydride was added dropwise at a temperature below 10° C. in a ratio of 1.1:1, and the resulting mixture was subjected to an acylation reaction. After the acylation reaction continued at a temperature below 10° C. for 2 h, a quenching reaction was conducted with water in a ratio of 0.25:1. The organo-tin compound was extracted with cyclohexane in a ratio of 1:1. The resulting sucrose-6-acetate solution was analyzed by HPLC.

The analysis results (those in parentheses were normalization results) are as follows. Where, normalization means that, during an HPLC analysis process, the sum of all substances is specified as 100%, and the percentage of each substance to all substances is determined according to the peak area.

TABLE 1

HPLC analysis results of the sucrose-6-acetate solution obtained in Example 1

| Component | One dehydration reaction | Two dehydration reactions | Three dehydration reactions |
|---|---|---|---|
| Sucrose-6-acetate | 7.09% (67.56) | 9.68% (87.84%) | 10.30% (89.9%) |
| Sucrose diacetate | 0.44 (4.21%) | 0.64% (5.86%) | 0.98% (8.6%) |
| Sucrose | 0.58% (15.56%) | 0.57% (5.21%) | 0.03% (0.24%) |

Example 2

1,000 g of sucrose and 2,000 g of 1,3-diacyloxy-1,1,3,3-tetra-(hydrocarbyl)distannoxane were dissolved in 10 L of DMF (a polar aprotic solvent), and then 1 L of cyclohexane (a non-polar solvent) was supplemented, obtaining a reaction solution of sucrose and an organo-tin compound.

The specific process parameters of this example were as follows: atomization dehydration reactor: low-temperature vacuum spray dryer, with a model of JOYN-1000T; sample injection volume: 10 mL/min; atomization nozzle caliber: 0.5 mm; temperature of fed reaction solution: 80° C.; gasified cyclohexane injection volume of a vaporizer: 2,000 mL/min, temperature: 90° C.; and the system pressure in the atomization dehydration reactor: 50 KPa.

The atomization dehydration operation and subsequent acylation treatment in this example were the same as those in Example 1. The resulting sucrose-6-acetate solution was analyzed by HPLC. The HPLC analysis results (those in parentheses were normalization results) are as follows:

TABLE 2

HPLC analysis results of the sucrose-6-acetate solution obtained in Example 2

| Component | One dehydration reaction | Two dehydration reactions | Three dehydration reactions |
|---|---|---|---|
| Sucrose-6-acetate | 6.68% (69.56%) | 7.94% (85.36%) | 8.30% (90.1%) |
| Sucrose diacetate | 0.42% (4.33%) | 0.61% (6.56%) | 0.69% (7.52%) |
| Sucrose | 1.27% (13.25%) | 0.33% (3.54%) | 0.03% (0.35%) |

Example 3

1,000 g of sucrose and 1,000 g of dibutyltin oxide were dissolved in 10 L of DMF (a polar aprotic solvent), and then 1 L of toluene (a non-polar solvent) was supplemented, obtaining a reaction solution of sucrose and an organo-tin compound.

The specific process parameters of this example were as follows: atomization dehydration reactor: low-temperature vacuum spray dryer, with a model of JOYN-1000T; sample injection volume: 10 mL/min; atomization nozzle caliber: 0.5 mm; temperature of fed reaction solution: 80° C.; gasified toluene injection volume of a vaporizer: 2,000 mL/min, temperature: 120° C.; and the system pressure in the atomization dehydration reactor: 50 KPa.

The atomization dehydration operation and subsequent acylation treatment in this example were the same as those in Example 1. The resulting sucrose-6-acetate solution was analyzed by HPLC. The HPLC analysis results (those in parentheses were normalization results) are as follows:

TABLE 3

HPLC analysis results of the sucrose-6-acetate solution obtained in Example 3

| Component | One dehydration reaction | Two dehydration reactions | Three dehydration reactions |
|---|---|---|---|
| Sucrose-6-acetate | 8.90% (72.35%) | 9.56% (86.63%) | 10.31% (89.21%) |
| Sucrose diacetate | 0.66% (5.34%) | 0.75% (6.79%) | 1.03% (8.95%) |
| Sucrose | 1.35% (10.98%) | 0.26% (2.32%) | 0.03% (0.26%) |

Example 4

1,000 g of sucrose and 2,000 g of 1,3-diacyloxy-1,1,3,3-tetra-(hydrocarbyl)distannoxane were dissolved in 10 L of DMF (a polar aprotic solvent), and then 1 L of toluene (a non-polar solvent) was supplemented, obtaining a reaction solution sucrose and an organo-tin compound.

The specific process parameters of this example were as follows: atomization dehydration reactor: low-temperature vacuum spray dryer, with a model of JOYN-1000T: sample injection volume: 10 mL/min; atomization nozzle caliber: 0.5 mm; temperature of fed reaction solution: 80° C.; dry nitrogen injection volume of a vaporizer: 2,000 mL/min, temperature: 120° C.; and the system pressure in the atomization dehydration reactor: 50 KPa.

The atomization dehydration operation and subsequent acylation treatment in this example were the same as those in Example 1. The resulting sucrose-6-acetate solution was analyzed by HPLC. The HPLC analysis results (those in parentheses were normalization results) are as follows:

TABLE 4

HPLC analysis results of the sucrose-6-acetate solution obtained in Example 4

| Component | Three dehydration reactions | Five dehydration reactions | Ten dehydration reactions |
|---|---|---|---|
| Sucrose-6-acetate | 8.84% (83.36%) | 8.98% (88.96%) | 9.50% (89.65%) |
| Sucrose diacetate | 0.67% (6.32%) | 0.77% (7.65%) | 0.92% (8.67%) |
| Sucrose | 0.67% (6.35%) | 0.05% (0.52%) | 0.03% (0.3%) |

Comparative Example 1

According to a mass ratio of sucrose, 1,3-diacetoxy-1,1,3,3-tetrabutyltistannoxane and DMF of 1:2:10, they were prepared into 300 kg of a reaction solution, and the reaction solution was heated at 90° C. and dissolved, obtaining a reaction mixed solution.

The reaction mixed solution was dehydrated by means of falling liquid in a packed tower. The packed tower has a diameter of 40 mm and was packed with a 3×8 glass spring packing at a packing height of 1 m, which is equivalent to 10-stage tower plates.

The reaction mixed solution prepared above was fed from an inlet of the top of the packed tower. The negative pressure was kept at 0.5 kPa. At the same time, a cyclohexane vapor (100° C., 4 atm) was fed from a flask gas inlet at the bottom of the packed tower. The reaction mixed solution was reacted with the cyclohexane vapor in countercurrent contact. The distillate (a vapor containing cyclohexane, water, and DMF) discharged from the top of the packed tower was condensed and collected, and can be recycled after removing water by drying.

The liquid sample was collected in a flask at the bottom of the packed tower. The obtained product was transparent and light-amber. The retention time of the reaction solution in a gas-liquid exchange reactor was about 1 min.

The resulting solution contains 10% sucrose by calculation. Acetic anhydride was added dropwise at a temperature below 10° C. in a ratio of 1:1.1, and the resulting mixture was subjected to an acylation reaction. After the acylation reaction continued at a temperature below 10° C. for 2 h, a quenching reaction was conducted with water in a ratio of 0.25:1. The organo-tin compound was extracted with cyclohexane in a ratio of 1:1. The resulting sucrose-6-acetate solution was analyzed by HPLC. The analysis results of the products are as follows:

a. sucrose-6-acetate: 7.56% (72.05%, normalized);
b. diacetate: 0.46% (4.36%, normalized); and
c. sucrose: 2.39% (22.76%, normalized).

It can be seen from Examples 1 to 4 and Comparative Example 1 that, compared with the packing and falling liquid production method used in Comparative Example 1, the sucrose-6-ester prepared by the method for preparing a sucrose-6-ester provided in the present disclosure has a higher yield and a lower occurrence probability of side reaction, and exhibits complete sucrose reaction. It can be seen from the yield of sucrose-6-acetate, in some examples of the present disclosure, the yield can reach 8.30% (90.1%, normalized), while in Comparative Example 1, the yield is 7.56% (72.05%, normalized); that is, the yield of the sucrose-6-ester in the present disclosure is significantly higher than that in the prior art. Similarly, it can be seen from the contents of diacetate and sucrose in the reaction products that in the present disclosure, the occurrence probability of side reaction is significantly reduced, and the conversion of sucrose is more thorough.

In summary, in the present disclosure, a sucrose-6-ester is prepared by the atomization drying method. The droplets atomized by the reaction solution have a huge SSA, such that the rapid and efficient dehydration of the esterification reaction can be achieved in a very short period of time, the sucrose organic tin ester intermediate can be efficiently prepared, and the decomposition of saccharides in a system and the occurrence of side reactions can be greatly reduced. Through repeated cyclic dehydration reactions of the sucrose organic tin ester solution and low energy consumption, the product has a high product yield and strong selectivity, the sucrose reaction degree is more thorough, and the conversion degree of sucrose is obviously improved. In addition, the overall energy consumption of the reaction is low and the energy consumption is significantly saved. Thus, the method makes it possible to overcome the shortcomings of the traditional methods for preparing a sucrose-6-ester, such as a long time, high energy consumption, many side reactions, complicated operations, and low yield, and is especially suitable for large-scale industrial production.

The above are merely specific embodiments of the present disclosure. Under the above teaching of the present disclosure, those skilled in the art may make other improvements or variations on the basis of the above examples. It should be understood by those skilled in the art that the above detailed description is merely intended to better explain the purpose of the present disclosure, and the protection scope of the present disclosure shall be subject to the protection scope of the claims.

In addition, those skilled in the art can understand that although some embodiments described herein include some features included in other embodiments but not others, the combination of features of different examples is meant to fall within the scope of the present disclosure and to form different embodiments. For example, in the following claims, any one of the claimed embodiments can be used in any combination.

What is claimed is:

1. A method for preparing a sucrose-6-ester, comprising:
preparing a reaction solution, comprising heating and dissolving sucrose and an organo-tin compound in a polar aprotic solvent, and adding a non-polar solvent thereto to obtain a reaction solution;
atomizing, comprising atomizing the reaction solution to form droplets;
dehydrating, comprising thoroughly mixing and contacting the droplets with a gasified dehydration medium such that the droplets undergo a dehydration reaction to obtain an intermediate mixture containing sucrose organic tin ester droplets;
separating, comprising separating the intermediate mixture to obtain a sucrose organic tin ester solution and a dehydrated gas-liquid mixture;
circulating, comprising recovering the sucrose organic tin ester solution obtained in the separating step and cycling to the atomizing and dehydrating steps several times; and
acylating, comprising subjecting an organic acid anhydride to an acylation reaction with the sucrose organic tin ester solution to obtain the sucrose-6-ester.

2. The method according to claim 1, wherein in the circulating step, the cycling is conducted 2 to 10 times.

3. The method according to claim 1, wherein the organo-tin compound is any one or more selected from the group consisting of 1,3-dihydrocarbyloxy-1,1,3,3-tetra-(hydrocarbyl)distannoxane, tin di(hydrocarbyl)oxide, 1,3-diacyloxy-1,1,3,3-tetra-(hydrocarbyl)distannoxane, 1-acyloxy-1,1,3,3-tetra-(hydrocarbyl)distannoxane, 1,3-diacetoxy-1,1,3,3-tetrabutyldistannoxane; wherein the hydrocarbyloxy is selected from the group consisting of alkoxy and phenoxy; the alkoxy is selected from the group consisting of methoxy, ethoxy, n-propoxy, n-butoxy, n-pentoxy, and n-hexoxy, and methoxy; the hydrocarbyl is selected from the group consisting of alkyl, cycloalkyl, aryl, aralkyl, and n-butyl;

the polar aprotic solvent is any one or more selected from the group consisting of dimethyl sulfoxide (DMSO), N-methylpyrrolidone (NMP), N,N-dimethylacetamide (DMA), hexamethylphosphoramide (HMPA), and N,N-dimethylformamide (DMF); and the non-polar solvent is any one selected from the group consisting of cyclohexane, hexane, n-heptane, iso-octane, benzene, toluene, chloroform, carbon tetrachloride, hexane, ethyl acetate, and methyl acetate.

4. The method according to claim 3, wherein based on a mass of sucrose, a ratio of a mass of the organo-tin compound to the mass of sucrose is in a range of 0.3-3.0;

based on the mass of sucrose, a ratio of a volume of the polar aprotic solvent to the mass of sucrose is in a range of 2-20; and based on the volume of the polar aprotic solvent, a volume of the non-polar solvent is less than 30% of the volume of the polar aprotic solvent.

5. The method according to claim 3, wherein in the atomizing step, atomizing the reaction solution to form droplets comprises:

heating the reaction solution to 70° C. to 120° C., and pressurizing to 0.01 MPa to 3 Mpa for atomization to form droplets, wherein a number of the droplets with a particle size less than 10 μm in the droplets accounts for 90% or more of a total number of the droplets.

6. The method according to claim 1, wherein the dehydration medium is selected from the group consisting of nitrogen and a non-polar solvent, wherein the non-polar solvent is any one selected from the group consisting of cyclohexane, hexane, n-heptane, iso-octane, benzene, toluene, chloroform, carbon tetrachloride, hexane, ethyl acetate, and methyl acetate;

based on a total mass of sucrose, the polar aprotic solvent, and the polar aprotic solvent, a ratio of a mass of the dehydration medium to the total mass is in a range of 100:0.1 to 0.1:1;

the dehydration medium has a gasification temperature of 80° C. to 160° C., and a gasification pressure of 0.01 Mpa to 3.0 Mpa; and a contact time between the droplets and the gasified dehydration medium is 1 s to 10 min.

7. The method according to claim 1, wherein the organic acid anhydride is any one selected from the group consisting of acetic anhydride, butyric anhydride, benzoic anhydride, stearic anhydride, and lauric anhydride;

based on the mass of sucrose, a ratio of a mass of the organic acid anhydride to the mass of the sucrose is in a range of 0.6-3.0; and the acylation reaction is conducted at a temperature of 0° C. to 50° C.

8. The method according to claim 1, further comprising:

Recycling, comprising subjecting the dehydrated gas-liquid mixture obtained in the separating step to gas-liquid separation to obtain a liquid substance and a gaseous substance, merging the liquid substance into the sucrose organic tin ester solution, and recovering the gaseous substance.

9. The method according to claim 8, wherein in the circulating step, the cycling is conducted 2 to 10 times.

10. The method according to claim 8, wherein the organo-tin compound is any one or more selected from the group consisting of 1,3-dihydrocarbyloxy-1,1,3,3-tetra(hydrocarbyl)distannoxane, tin di(hydrocarbyl)oxide, 1,3-diacyloxy-1,1,3,3-tetra-(hydrocarbyl)distannoxane, and 1-acyloxy-1,1,3,3-tetra-(hydrocarbyl)distannoxane, and 1,3-diacetoxy-1,1,3,3-tetrabutyldistannoxane; wherein the hydrocarbyloxy is selected from the group consisting of alkoxy and phenoxy; the alkoxy is selected from the group consisting of methoxy, ethoxy, n-propoxy, n-butoxy, n-pentoxy, and n-hexoxy; the hydrocarbyl is selected from the group consisting of alkyl, cycloalkyl, aryl, and aralkyl;

the polar aprotic solvent is any one or more selected from the group consisting of dimethyl sulfoxide (DMSO), N-methylpyrrolidone (NMP), N,N-dimethylacetamide (DMA), hexamethylphosphoramide (HMPA), and N,N-dimethylformamide (DMF); and the non-polar solvent is any one selected from the group consisting of cyclohexane, hexane, n-heptane, iso-octane, benzene, toluene, chloroform, carbon tetrachloride, hexane, ethyl acetate, and methyl acetate.

11. The method according to claim 8, wherein the dehydration medium is selected from the group consisting of nitrogen and a non-polar solvent, wherein the non-polar solvent is any one selected from the group consisting of cyclohexane, hexane, n-heptane, iso-octane, benzene, toluene, chloroform, carbon tetrachloride, hexane, ethyl acetate, and methyl acetate;

based on a total mass of sucrose, the polar aprotic solvent, and the polar aprotic solvent, a ratio of a mass of the dehydration medium to the total mass is in a range of 100:0.1 to 0.1:1;

the dehydration medium has a gasification temperature of 80° C. to 160° C., and a gasification pressure of 0.01 MPa to 3.0 MPa; and a contact time between the droplets and the gasified dehydration medium is 1 s to 10 min.

12. The method according to claim 8, wherein the organic acid anhydride is any one selected from the group consisting of acetic anhydride, butyric anhydride, benzoic anhydride, stearic anhydride, and lauric anhydride;

based on the mass of sucrose, a ratio of a mass of the organic acid anhydride to the mass of the sucrose is in a range of 0.6-3.0; and the acylation reaction is conducted at a temperature of 0° C. to 50° C.

13. A method for preparing a sucrose-6-ester, wherein in the method, an atomization dehydration reactor is used, and the atomization dehydration reactor comprises a reactor body that is provided with a drying chamber and a first discharge chamber sequentially from top to bottom, wherein the drying chamber is provided with an atomization nozzle, and the atomization nozzle is connected with a liquid material tank through an on-line heater and an infusion pressure pump successively; a top of the drying chamber is further provided with a gas distributor, and a vaporizer equipped with a gas filter is connected to an inlet of the gas distributor; and one end of the first discharge chamber is provided with a first gas discharge pipe, and the other end is provided with a first liquid discharge port; and the method comprises:

preparing a reaction solution, comprising heating and dissolving sucrose and an organo-tin compound in a polar aprotic solvent, and adding a non-polar solvent thereto to obtain a reaction mixed solution;

atomizing, comprising adding the reaction mixed solution to the liquid material tank, heating by the on-line heater and pressurizing by the infusion pressure pump, introducing into the atomization nozzle and atomizing into droplets, and spraying the droplets into the drying chamber;

dehydrating, comprising adding a dehydration medium to the vaporizer, filtering, heating, and pressurizing to form a gasified dehydration medium, and introducing the gasified dehydration medium into the gas distributor, evenly distributing by the gas distributor, and introducing into the drying chamber, wherein the droplets and the gasified dehydration medium are thoroughly mixed and contacted in the drying chamber, such that the droplets undergo a dehydration reaction to obtain an intermediate mixture containing sucrose organic tin ester droplets;

separating, comprising subjecting the intermediate mixture to gas-liquid separation in the first discharge chamber to obtain a sucrose organic tin ester solution and a dehydrated gas-liquid mixture, discharging the sucrose organic tin ester solution from the first liquid discharge port of the first discharge chamber, and discharging and recovering the dehydrated gas-liquid mixture from the first gas discharge pipe of the first discharge chamber;

circulating, comprising recovering the sucrose organic tin ester solution obtained in the separating step to the liquid material tank, such that the sucrose organic tin ester solution is cycled through the atomizing and dehydrating steps several times;

or, a plurality of the atomization dehydration reactors are sequentially provided in series at the first liquid discharge port arranged at the other end of the first discharge chamber, and after being discharged from the first liquid discharge port of the first discharge chamber, the sucrose organic tin ester solution successively passes through the plurality of atomization dehydration reactors provided in series, such that the sucrose organic tin ester solution is cycled through the atomizing and dehydrating steps; and acylating, comprising subjecting an organic acid anhydride to an acylation reaction with the sucrose organic tin ester solution to obtain the sucrose-6-ester.

14. The method according to claim 13, wherein the atomization dehydration reactor further comprises a cyclone separator, and the gas discharge pipe of the first discharge chamber is connected to an inlet of the cyclone separator; the cyclone separator is provided with a separation chamber and a second discharge chamber sequentially from top to bottom; one end of the separation chamber is provided with a gas outlet that is connected to an induced drag fan; and the second discharge chamber is provided with a second liquid discharge port; and the method further comprises:

recycling, comprising subjecting the dehydrated gas-liquid mixture obtained in the separating step to gas-liquid separation to obtain a liquid substance and a gaseous substance, merging the liquid substance into the sucrose organic tin ester solution, and recovering the gaseous substance.

15. The method according to claim 14, wherein in the circulating step, the cycling is conducted 2 to 10 times.

16. The method according to claim 13, wherein in the circulating step, the cycling is conducted 2 to 10 times.

* * * * *